United States Patent
Bates

(10) Patent No.: US 7,667,839 B2
(45) Date of Patent: Feb. 23, 2010

(54) AEROSOL PARTICLE SENSOR WITH AXIAL FAN

(75) Inventor: Thomas Bates, Westminster, CO (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 11/393,475

(22) Filed: Mar. 30, 2006

(65) Prior Publication Data

US 2007/0229825 A1 Oct. 4, 2007

(51) Int. Cl.
*G01N 21/00* (2006.01)
(52) U.S. Cl. ......... 356/337; 356/338
(58) Field of Classification Search ......... 356/337, 356/432, 437
See application file for complete search history.

(56) References Cited

U.S. PATENT DOCUMENTS

| | | | | |
|---|---|---|---|---|
| 4,746,215 | A | | 5/1988 | Gross |
| 5,519,490 | A | * | 5/1996 | Nakata et al. ......... 356/338 |
| 5,600,438 | A | * | 2/1997 | Kreikebaum et al. ......... 356/339 |
| 5,825,487 | A | * | 10/1998 | Felbinger et al. ......... 356/338 |
| 5,889,589 | A | | 3/1999 | Sandberg |
| 6,061,132 | A | | 5/2000 | Girvin et al. |
| 6,167,107 | A | * | 12/2000 | Bates ......... 377/10 |
| 6,386,015 | B1 | * | 5/2002 | Rader et al. ......... 73/31.05 |
| 6,867,413 | B2 | * | 3/2005 | Basch et al. ......... 250/255 |
| 6,885,440 | B2 | * | 4/2005 | Silcott et al. ......... 356/73 |
| 2003/0052281 | A1 | * | 3/2003 | Rader et al. ......... 250/461.1 |
| 2004/0045376 | A1 | | 3/2004 | Van Netten |

FOREIGN PATENT DOCUMENTS

EP 1126021 8/2001

OTHER PUBLICATIONS

International Search report by EPO corresponding to PCT/US2007/007158, Mailed Sep. 13, 2007.

* cited by examiner

*Primary Examiner*—Roy Punnoose
(74) *Attorney, Agent, or Firm*—Greenlee, Winner and Sullivan, P.C.

(57) ABSTRACT

A particle sensor for optically detecting an unconstrained particle suspended in a flowing gas includes a sample chamber having a gas inlet and a gas outlet; a gas flow system for flowing said gas from said gas inlet through said sample chamber to said gas outlet, a source of light; an optical system directing said light through said sample chamber, an optical collection system located to collect light scattered by said particles in the gas, and a detection system located to detect the collected light. The total pressure drop through said gas flow system is 3 inches of water or less. The gas flow system includes an axial fan, which may be a high static pressure fan or a counter-rotating fan. In a 1.0 CFM system, the gas inlet nozzle has an area of 25 square millimeters or more.

29 Claims, 3 Drawing Sheets

AEROSOL PARTICLE SENSOR WITH AXIAL FAN

FIELD OF THE INVENTION

The invention in general relates to systems that utilize light scattering principles to sense undesirable single particles in gases, which systems are generally referred to in the art as optical particle counters, and more particularly, the airflow systems in such particle counters.

BACKGROUND OF THE INVENTION

It is well known that in industries such as high-tech electronics and pharmaceutical manufacturing it is necessary to prevent contamination by small particles. This need has given rise to the development of optical particle counters in which fluid flows through an optical sensor which detects the presence of contaminant particles. Particle counters which detect particles in air or other gas are sometimes referred to as "aerosol particle counters". Standards generally require that aerosol particle counters monitor the entire volume of gas flowing through the sensor. Particle counters that monitor the entire volume of gas flowing through the sensor are referred to in the micro-contamination industry as "volumetric". The micro-contamination industry has evolved two distinct methodologies for continuous volumetric aerosol particulate monitoring of environments. One method involves the use of an aerosol manifold system. The use of a manifold system allows a single particle counter to sequentially monitor multiple sample locations in an environment. This allows the cost of the particle counter, the manifold, and the system vacuum pump to be shared among multiple sample points. A major drawback of this method is the transport loss of large particles down the required lengthy sample tubing runs. This is unavoidable, as all sample points must be routed to the single particle counter. Some sample lines may reach over a hundred feet in length. Another major disadvantage of this method is the sample points can only be evaluated one at a time; therefore, real-time monitoring of all sample locations is not possible.

The second common methodology requires the use of dedicated particle counters at each of the required sample points. This method provides continuous real-time monitoring of all sample locations and also eliminates large particle transport tubing loss, as a particle sensor can be placed at or near each required sample location, thus minimizing sample tubing length. However, this method requires a large number of particle counters and, for large plants, can be quite expensive. The response to this problem has led to the development of particle sensors. A particle sensor generally will have no external display, keyboard, internal airflow pump, or variable flow control devices. This minimizes the cost of the sensor, but requires the end-user to provide an external vacuum pumping system. These sensors are most commonly 1.0 CFM (cubic feet per minute) or 0.1 CFM flow rate. With no internal airflow pump or variable flow control and measurement system, particle sensors generally utilize a critical flow orifice to control the sample flow rate. The use of a critical flow orifice to control volumetric flow rate has been well established as explained in Willeke/Baron, *"Aerosol Measurement"* and Hinds, *"Aerosol Technology"*. The required critical pressure drop needed is given by the following equation:

$$P_V/P_a = [2/(k+1)]^{k/k-1}$$

where $P_V$=Pressure on vacuum side of critical flow orifice;
$P_a$=Pressure on upstream side of critical flow orifice;
K=Gas specific heat ratio=7/5 for diatomic gases=1.4.

Substituting 1.4 for k yields the simplified equation:

$$P_V/P_a = 0.53.$$

At standard conditions, $P_a$=14.7 psi. Therefore, the required critical pressure drop at standard conditions is 7.791 psi (15.9" Hg). Measured in inches of water, this is 215.6 inches. That is, a pressure of 1 inch of water is equal to 7.791/215.6 psi or 0.0361 psi. Since, 1 psi is equal to 6,894.76 pascals (Pa). 1 inch of water is equal to 249.15 Pa or 0.24915 kPa, 2 inches of water is equal to 0.4983 kPa, and 3 inches of water is equal to 0.74745 kPa.

At standard conditions, a critical flow orifice will maintain constant volumetric flow when the downstream vacuum level is greater than 15.9 inches Hg. Under these conditions, the velocity in the throat of the orifice is the speed of sound, and a further increase in the downstream vacuum level does not increase the velocity through the throat. This requires the user to provide a vacuum pumping system that can maintain a minimum of 15 inches to 17 inches Hg vacuum level at the particle sensor's specified flow rate.

The requirement for a vacuum pump capable of maintaining >15 inches Hg for even a single 1.0 CFM particle sensor limits the available options of pump choice to a positive displacement pump such as a carbon vain rotary design. These pumps are quite large and consume greater than 100 Watts of power. As the user will typically install multiple particle sensors, the number of particle sensors in use will increase the pumping system requirements. It is quite common for the pumping system to weigh several hundred pounds and have power consumption measured into the thousands of watts. In addition, vacuum lines must be installed to run from the central vacuum pump to each and every sensor installed into the system. The final flow system install cost is typically $500 to $700 per instrument.

In recent years, particle counter manufacturers have begun to offer particle sensors that include internal pumps or blowers that are controlled by a closed loop flow measurement and control device. With the addition of an intelligent flow control system, the critical flow orifice may be removed. This eliminates the dominant pressure drop in the system and leaves the pressure drop of the particle sensor itself in addition to any desired inlet tubing. Current particle sensor pressure drops range from approximately 3 inches to 50 inches of water. Typical inlet tubing pressure drop is 2 inches to 10 inches of water for inlet tubing lengths reaching up to 5 feet in length. The total system pressure drop is then typically 5 inches to 60 inches of water, which includes the sensor pressure drop plus the inlet tubing pressure drop.

With the maximum pressure drop now significantly lowered from the 215.6 inches of water of the critical flow orifice designs, it is possible to utilize air-moving devices other than positive displacement pumps. Radial and regenerative blowers are capable of moving air in the pressure ranges reaching up to 25 inches of water. These blowers can be controlled with a DC voltage, making them easy to integrate into a closed loop flow control system. Typically, they operate in the 25 W to 75 W power range, making them a lower power option than positive displacement pumps. See U.S. Pat. No. 6,167,107 issued Dec. 26, 2000. The major disadvantage of radial and regenerative blowers is their cost. As with particle sensors that utilize critical flow orifices, the final system install cost remains at $500 to $700 per sensor. Thus, while these systems provide continuous monitoring and do not require a massive airflow system, still there is no cost advantage to utilizing these types of blowers in a multiple particle sensor system.

Thus, there remains a need of a system and method of controlling volumetric flow rate in an aerosol particle sensor that would substantially reduce the final installation cost of a multiple sensor system and yet provide continuous monitoring at all critical locations in an environment.

BRIEF SUMMARY OF THE INVENTION

The present invention advances the art and helps to overcome the aforementioned problems by providing an optical particle sensor in which the total pressure drop through the system is 3 inches of water or less. In another aspect, the invention advances the art and helps to overcome the aforementioned problems by providing an optical particle counter that includes an axial fan. Preferably, the axial fan comprises a high static pressure fan or a counter-rotating fan. Preferably, the low pressure drop is accomplished by utilizing an inlet jet nozzle that is 4 $mm^2$ or more in a 0.1 CFM system and, alternatively, 25 $mm^2$ or more in a 1.0 CFM system.

The invention provides an optical particle sensor for optically detecting unconstrained particles suspended in a flowing gas, the optical particle sensor comprising: a sample chamber having a gas inlet and a gas outlet; a gas flow system for flowing the gas from the gas inlet through the sample chamber to the gas outlet; a source of light; an optical system directing the light through the sample chamber, an optical collection system located to collect light scattered by the particles in the gas flowing through the sample chamber, and a detection system located to detect light collected by the optical collection system, the detection system including an optical detector producing an electric signal characteristic of the particles; wherein the total pressure drop through the gas flow system is 3 inches of water or less. Preferably, the total pressure drop is 2 inches of water or less. More preferably, the total pressure drop is 1 inch of water or less. Preferably, the gas flow system comprises an axial fan. Preferably, the axial fan comprises a high static pressure fan or a counter-rotating fan. Preferably, the gas flow system has a gas flow of substantially 0.1 CFM (cubic feet per minute) and includes an inlet jet nozzle having a cross-sectional area of 4 $mm^2$ (millimeters squared) or larger. Preferably, the 0.1.0 CFM gas flow system comprises inlet tubing having an inner diameter of 6.4 mm or larger. Alternatively, the gas flow system has a gas flow of substantially 1.0 CFM (cubic feet per minute) and includes an inlet jet nozzle having a cross-sectional area of 25 $mm^2$ (millimeters squared) or larger. Preferably, the 1.0 CFM system comprises inlet tubing having an inner diameter of 9.5 mm or larger. Preferably, the 1.0 CFM comprises inlet tubing having an inner diameter of 12 mm or larger. More preferably, the 1.0 CFM gas flow system has a gas flow of substantially 1.0 CFM (cubic foot per minute) and includes an inlet jet nozzle having a cross-sectional area of 30 $mm^2$ (millimeters squared) or larger. Preferably, the source of light comprises a laser having a power of 50 milliwatts or greater. More preferably, the source of light comprises a laser having a power of 100 milliwatts or greater. The invention also provides an optical particle counter system including a plurality of particle sensors as described above.

The invention also provides an optical particle sensor for optically detecting unconstrained particles suspended in a flowing gas, the optical particle sensor comprising: a sample chamber having a gas inlet and a gas outlet; a gas flow system for flowing the gas from the gas inlet through the sample chamber to the gas outlet, the gas flow system including an axial fan; a source of light; an optical system directing the light through the sample chamber, an optical collection system located to collect light scattered by the particles in the gas flowing through the sample chamber, and a detection system located to detect light collected by the optical collection system, the detection system including an optical detector producing an electric signal characteristic of the particles. Preferably, the axial fan comprises a counter-rotating fan. Alternatively, the axial fan comprises a high static pressure fan.

In another aspect, the invention provides an optical particle sensor for optically detecting unconstrained particles suspended in a flowing gas, the optical particle sensor comprising: a sample chamber having a gas inlet and a gas outlet; a gas flow system for flowing the gas from the gas inlet through the sample chamber to the gas outlet; the gas flow system having a flow rate of substantially 0.1 CFM (cubic feet per minute) and a gas inlet jet nozzle having a cross-sectional area of 4 $mm^2$ (millimeters squared) or larger, a source of light; an optical system directing the light through the sample chamber, an optical collection system located to collect light scattered by the particles in the gas flowing through the sample chamber, and a detection system located to detect light collected by the optical collection system, the detection system including an optical detector producing an electric signal characteristic of the particles.

In a further aspect, the invention provides an optical particle sensor for optically detecting unconstrained particles suspended in a flowing gas, the optical particle sensor comprising: a sample chamber having a gas inlet and a gas outlet; a gas flow system for flowing the gas from the gas inlet through the sample chamber to the gas outlet, the gas flow system having a flow rate of substantially 1.0 CFM (cubic feet per minute) and a gas inlet jet nozzle having a cross-sectional area of 25 $mm^2$ (millimeters squared) or larger, a source of light; an optical system directing the light through the sample chamber, an optical collection system located to collect light scattered by the particles in the gas flowing through the sample chamber, and a detection system located to detect light collected by the optical collection system, the detection system including an optical detector producing an electric signal characteristic of the particles.

The invention also provides a method of detecting unconstrained particles in a flowing gas, the method comprising: flowing the gas containing the unconstrained particles using an axial fan; directing a laser beam through the gas flow, collecting light scattered by the particles in the gas; and detecting the collected light and outputting a signal that is characteristic of a parameter of the particles. Preferably, the flowing comprises using a counter-rotating fan or a high static pressure fan.

In yet another aspect, the invention provides a method of detecting unconstrained particles in a flowing gas, the method comprising: flowing the gas containing the unconstrained particles from a gas inlet through a sample chamber to a gas outlet with a total pressure drop of 3 inches of water or less; directing a laser beam through the gas flow, collecting light scattered by the particles in the gas; and detecting the collected light and outputting a signal that is characteristic of a parameter of the particles. Preferably, the flowing comprises flowing the gas through a total pressure drop of 2 inches of water or less. More preferably, the flowing comprises flowing the gas through a total pressure drop of 1 inch of water or less. Preferably, the directing comprises forming a laser beam having an effective beam height of 2.5 mm (millimeters) or greater. Preferably, the directing comprises forming a laser beam having a power of 50 milliwatts or greater.

The invention dramatically reduces the cost, size, and power consumption of optical particle sensors. In addition, whole plant particle counter systems are greatly simplified. The above and other advantages of the present invention may be better understood from a reading of the following description of the preferred exemplary embodiments of the invention taken in conjunction with the drawings in which:

DETAILED DESCRIPTION OF THE INVENTION

In this disclosure, the term "light" is not limited to visible radiation but is used in a broad sense meaning any electromagnetic radiation, including infrared, ultraviolet, extreme ultraviolet, and x-ray radiation. It should be noted that particle sensors and particle counters as disclosed herein are designed to be able to detect single particles which are unconstrained in a flowing gas as distinguished from other systems that detect and analyze the particles of the gas itself, clouds of particles suspended in a gas, or particles which are constrained in the gas, such as constrained to flow in a single line past a light beam. Those skilled in the art recognize that it is a much more difficult task to detect and size single particles flowing unconstrained in a gas, particularly particles of less than one micron in size; therefore, the art of particle counting involves different technology than these other particle detection and analysis systems.

An aerosol particle counter or sensor instrument utilizes a high static pressure fan or a counter-rotating fan module. The instrument is designed to minimize pressure drop, mainly by utilizing an inlet jet that has a large cross-sectional area. The pressure drop of the inlet jet is designed to be less than 1 inch of water at the desired flow rate. The entire system pressure drop is designed to be as little as possible.

The fan modules may be used in tandem with an intelligent flow control system. With an extended operating voltage range, these fan modules are ideally suited for use in a closed loop flow control system. The DC voltage may be varied to control flow rate. As the fan module may have separate DC voltage power to each of its fans, the fans may be independently controlled in order to extend the dynamic control range of the instrument. Multiple fan modules may be incorporated in order to extend the dynamic range or maximum capacity of the instrument.

Figure 1:
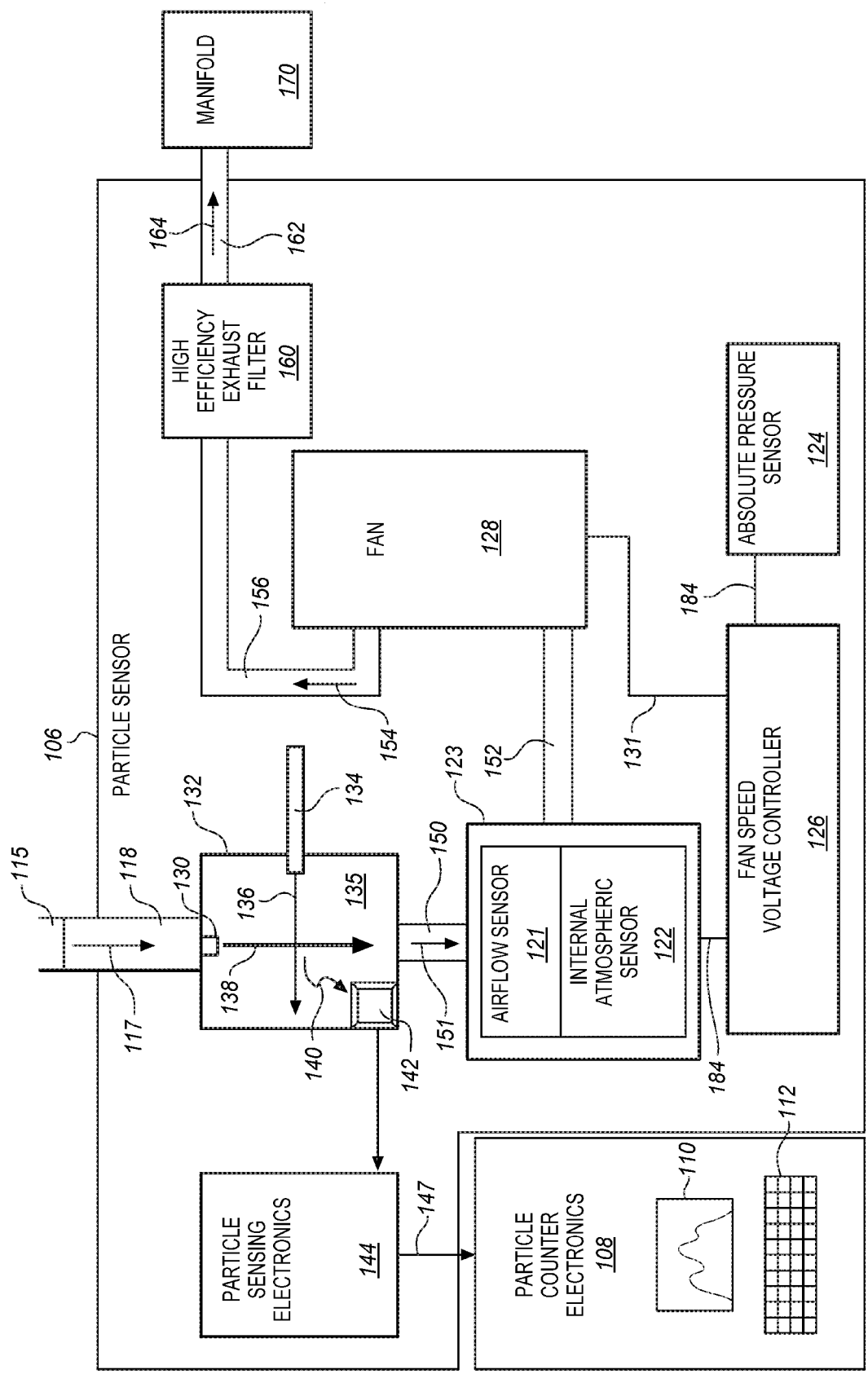
FIG. 1 shows a block diagram of a preferred embodiment of an optical particle sensor according to the invention.

FIG. 1 shows a particle counter including particle sensor 106 and particle counter electronics 108. Particle counter electronics 108 generally includes a display 110, an input device 112, such as a keyboard, and associated electronics to generate an output indicative of a parameter of the detected particles, such as the number of particles in different channels that include a range of particle sizes. These electronics are known in the art and will not be discussed in detail here.

Particle sensor 106 includes a flow cell 132, an airflow system, and particle sensing electronics 144. The airflow system includes inlet tubing 115, particle sensor airflow inlet tube 118, inlet jet nozzle 130, sample chamber 135, airflow sensor 121, internal atmospheric sensor 122, fan 128, fan speed controller 126, absolute pressure sensor 124, exhaust filter 160, airflow tube 150 connecting sample chamber 135 and sensors 121 and 122, airflow tube 152 connecting airflow sensor module 123 and fan 128, airflow tube 156 connecting fan 128 and filter 160, and outlet airflow tube 162. Airflow is as follows. Inlet air 117 is drawn into particle sensor 106 by fan 128 via tubing 115 and 118 and passes through inlet nozzle 130 to create airflow 138 in sample chamber 135. Air 151 from chamber 135 then passes into airflow sensor module 123 through tube 152 to fan 128. Fan 128 then exhausts exhaust air 154 through tube 156 to exhaust filter 160, and then exhaust air 164 exits the particle sensor 106 via outlet tube 162. Optionally, an exhaust manifold 170 may be connected to outlet tube 162 to provide additional direction and motive power to move the exhaust air out of the facility. As known in the art, pressure sensors 121 and 122 and absolute pressure sensor 124 are electrically connected to voltage controller 126, and voltage controller 126 is electrically connected to fan 128 to control the speed of fan 128 to ensure correct volumetric flow through the system, as discussed in more detail below. As known in the art, a laser 134 generates a laser beam 136 that illuminates flow 138 such that scattered energy 140, indicative of particles in flow 138, is detected by detector 142. Particle sensing electronics 144 amplifies the signal from detector 142 and provides an output on line 147 that is characteristic of a parameter of the detected particles, such as the number of particles. Signal 147 is analyzed by particle counter electronics 108 to provide the output data, such as particle count, in any conventional form required by the user. The design of flow cell 132 is described in more detail below in connection with FIG. 3.

Figure 2:
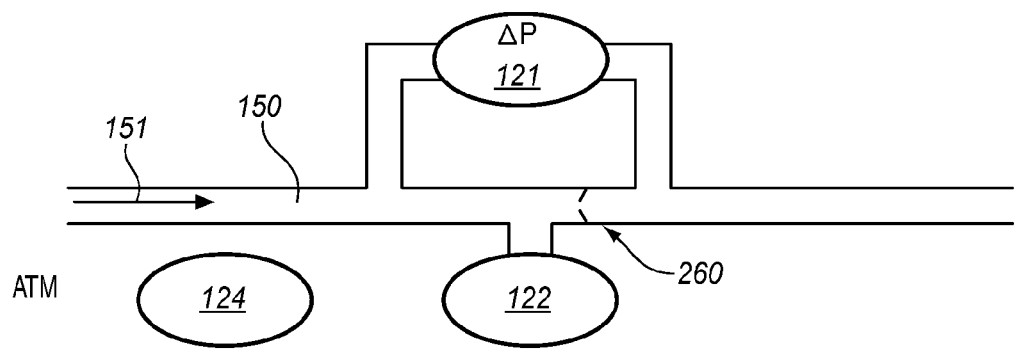
FIG. 2 illustrates a preferred embodiment of the pressure sensing techniques used in the system of FIG. 1.

Turning to FIG. 2, airflow sensor 121 measures airflow of air 151 across a restriction 260, and internal atmospheric sensor 122 measures pressure within sensor 106. Fan 128 draws air 151 through connecting tube 152 and exhausts air 154 through connecting tube 156, high efficiency exhaust filter 160, and outlet tube 162. The only exit of exhaust from particle sensor 106 is through filter 160, which cleans exhausted air 164 to reduce contamination within the system. Atmospheric pressure sensor 124 provides absolute pressure of ambient air 117 entering the system. Fan speed voltage controller 126 receives signals from sensors 121, 122, 124, via signal lines 184, and regulates the DC voltage, and thus the speed, of fan 128 through signal line 131 to control the volumetric flow rate of air 117 entering particle sensor 106.

FIG. 2 illustrates the principles of pressure sensing within sensor 106 to attain accurate volumetric flow rate within sensor 106. The flow rate (molecules/second) of air in sample tube 150 is measured by airflow sensor 121 across restricting orifice 260. Pressure sensor 122 measures the density of air inside sample tube 150. To attain the number of particulates at a desired volumetric flow, volumetric flow is determined by the flow rate and the atmospheric pressure as provided by airflow sensor 121 and pressure sensor 122, respectively. Pressure sensor 122 can be located elsewhere within system 100; however, a more accurate volumetric flow rate can be determined with pressure sensor 122 locally in sensor 106. More particularly, variable speed fan 128, as in FIG. 1, is used as the air-moving device within sensor 106. Differential airflow pressure sensor 121 in tandem with restricting orifice 260 measures the differential pressure drop across orifice 260 caused by airflow through orifice 260. Pressure sensor 122 measures the absolute air pressure directly upstream of restricting orifice 260. Absolute pressure sensor 124 measures the absolute air pressure of ambient air 117. Fan controller 126 interprets the information provided by pressure sensors 121, 122, 124 and derives an output signal, on signal line 131, that controls the speed of fan 128. Thus, the system provides a closed loop feedback control of fan 128.

Preferably, the airflow system provides an accurate 0.1 or 1.0 CFM volumetric flow rate as sampled from the ambient enviroument (i.e., the source of air 117). The system is intended to be used at elevations ranging approximately from sea level to 10,000 feet. The differential pressure signal, ΔP, generated by sensor 121 is proportional to the flow rate through particle sensor 106; however, the Bernoulli equation requires that the air density at sensor 121 be known in order to derive the actual volumetric flow rate. Pressure sensor 122 is used to measure this air density.

Pressure drops in the upstream flow of pressure sensor 122 causes the air density at its location to be slightly different than at the ambient environment of air 117. Therefore, the pressure ratio (pressure from pressure sensor 122 divided by pressure from pressure sensor 124) is interpreted to maintain the required volumetric flow rate at airflow sensor module 123, corresponding to 1.0 CFM or 0.1 CFM volumetric flow rate drawn from the ambient environment. Thus, the airflow system produces an accurate 0.1 to 1.0 CFM volumetric flow rate at the current ambient environment conditions as compensated for varying air density, due to site elevation, and local air pressure changes, due to environmental conditions.

The following equations are useful in determining the volumetric flow rate in the discussion above:

Ideal Gas Law:

$$\rho = PM/RT$$

where
  ρ=Density (kg/m$^3$)
  P=Pressure (kPa)
  M=Molar mass of air (28.97 kg/kmol)
  R=Universal Gas Constant (8.314 kJ/kmol·K)
  T=Temperature (° K)

Bernoulli Equation:

$$Q = k \cdot [(2 \cdot \Delta P)/\rho]^{1/2}$$

where
  Q=Volumetric Flow
  k=empirically determined constant
  ΔP=Differential pressure
  ρ=Density Simplified Equation for Volumetric Flow, Q, within Sensor 106:

$$Q = k \cdot [(P_{APSO} \cdot P_{DPS})^{1/2} \div P_{APSE}]$$

where
  Q=Ambient Volumetric Flow
  k=empirically determined constant
  $P_{APSO}$=Pressure of pressure sensor 124
  $P_{DPS}$=Differential pressure of airflow sensor 121
  $P_{APSE}$=Pressure of pressure sensor 122

Preferably, pressure sensor 121 is a Honeywell Model DCXL01DV differential pressure sensor or an Allsensor miniature amplified low pressure sensor Model I inch-G-P4V-Mini. For further discussion of flow control, see, for example, U.S. Pat. No. 6,167,107 issued Dec. 26, 2000 to Thomas Bates et al., which is hereby incorporated by reference to the same extent as though fully disclosed herein.

Figure 3:
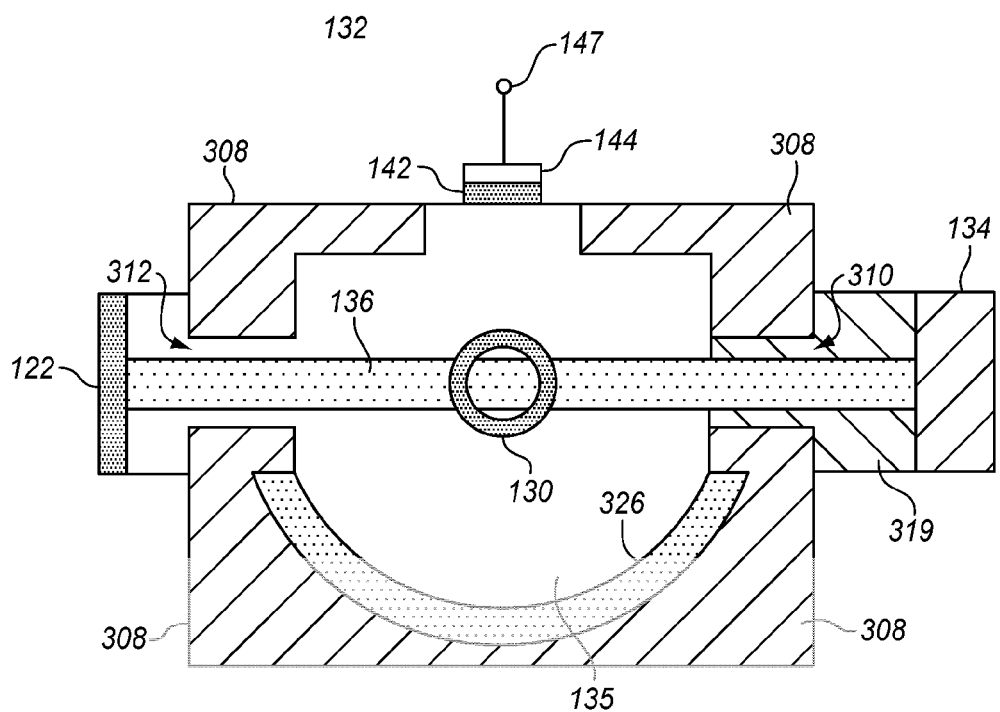
FIG. 3 illustrates the flow cell and detection optics of the optical particle sensor of FIG. 1 showing the arrangement of the inlet jet and laser beam.

Turning to FIG. 3, a flow cell 132 according to the preferred embodiment of the invention is shown. Flow cell 132 includes flow cell housing 308, flow cell window 319, laser beam entrance aperture 310, laser beam exit aperture 312, and mirror 326. Beam 136 is generated by laser 134, passes through window 319 and entrance aperture 310 into sample chamber 135, and exits flow cell 132 through exit aperture 312. As indicated in connection with FIG. 1, in chamber 135 laser beam 136 passes through a gas flow 138 exiting from inlet jet nozzle 130 and particles within flow 138 scatter the laser light. Light scattering in the downward direction in FIG. 3 is reflected toward detector 142 by mirror 326. Mirror 326 and any associated collection optics comprise a scattered light collection system. Light remaining in laser beam 136 is absorbed in beam dump 122. The scattered light is detected by detector 142, a detector signal is processed by electronics 144, and a signal characteristic of a parameter of the particles in flow 138 is output at 147. Detector 142 and electronics 144 comprise a scattered light detection system. As will be discussed below, nozzle 130 and laser beam 136 according to the invention are significantly larger than the nozzles and laser beams used in particle counters and particle sensors in the prior art, thus permitting a much lower pressure drop and a different type of fan 128 than used in prior art particle sensors and particle counters.

Figure 4:
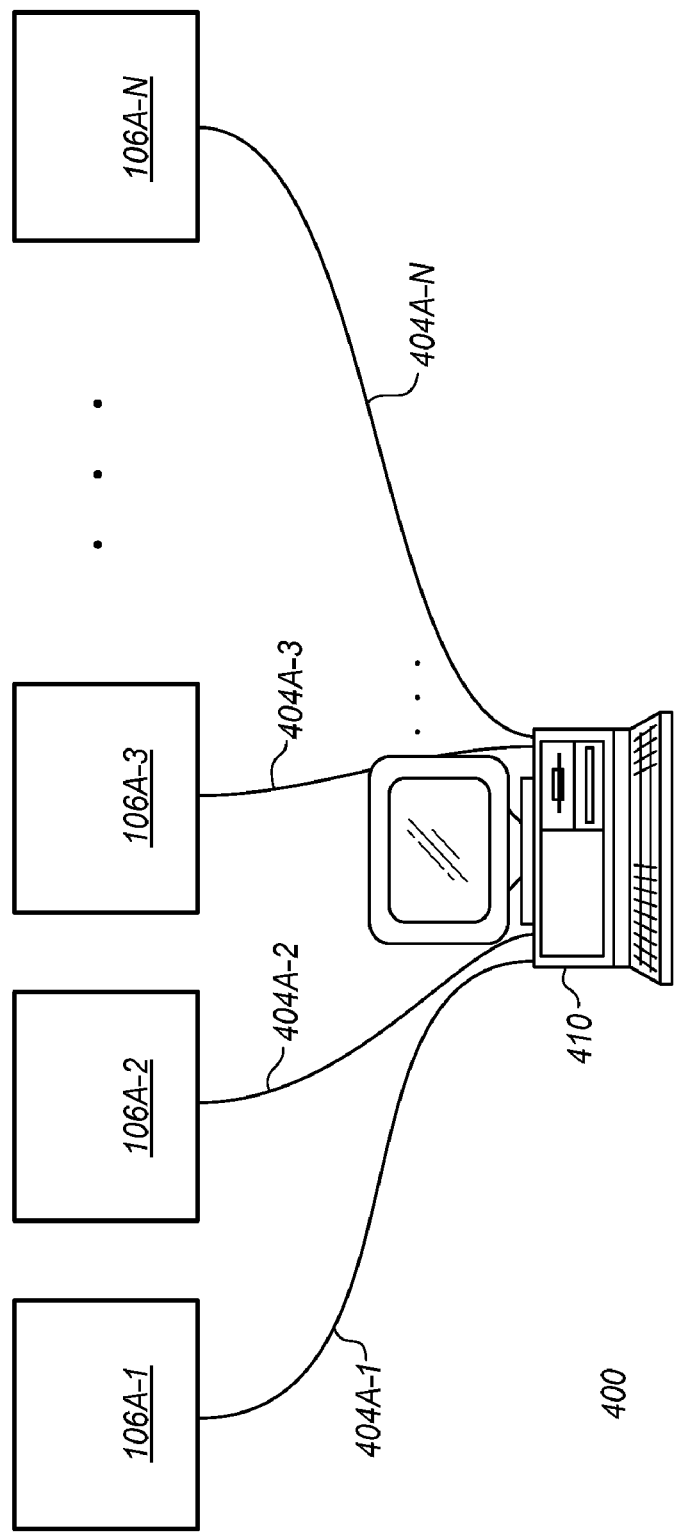
FIG. 4 is a block diagram of the preferred embodiment of an optical particle counter system employing a plurality of the optical particle sensors of FIG. 1.

FIG. 4 shows a particle counter system 400 according to the invention as may be employed in an environment such as a manufacturing plant. System 400 includes a plurality of particle sensors 106A-1, 106A-2, and 106A-3 through 106A-N, where N is an integer equal to 2 or larger, and a computer 410. In some embodiments, particle sensors 106A-1, 106A-2, and 106A-3 through 106A-N may be replaced by particle counters. Particle sensors 106A-1, 106A-2, and 106A-3 through 106A-N are connected to computer 410 via electronic connectors 404A-1, 404A-2, and 404A-3 through 404A-N, each of which may be a cable, either parallel or serial, a wireless connection, the Internet, or any other method of electronically connecting to a computer. Preferably, each of the particle sensors 106A-1, 106A-2, and 106A-3 through 106A-N is a particle sensor 106 as shown in FIG. 1. Computer 410 may be a personal computer, a workstation, or other computer with particle counting software installed as known in the art.

A feature of the invention is that particle sensor 106 according to the invention has an extremely low pressure drop, preferably of less than 5 inches of water, more preferably of less than 3 inches of water, and most preferably of less than 2 inches of water. This permits use of an axial fan as an air movement device. As known in the fan art, axial fans move air in a direction essentially parallel to the axis of rotation of the fans. Examples of the preferred axial fans are high static pressure fans and counter-rotating fans. These devices are very effective at moving air in the low pressure drop range. As known in the art, high static pressure fans are axial fans that utilize guide fins to change at least a portion of the rotational energy of the air to energy along the axial direction. An example of a high static pressure fan is the Sunon Model PMD1204PQB1-A. This fan can generate a differential pressure of approximately 0 to 1.25 inches of water. Two examples of commercially available counter-rotating fan modules are the Sanyo Denki Sun Ace Model 9CR0412S501 and the Sunon Model PMD1204PPB1-A. Counter-rotating fans utilize a pair of rotating fan blades, one fan blade rotating in a clockwise direction and the other fan blade rotating in a counter-clockwise direction. Preferably, each fan blade also rotates at a different speed. For example, the Sunon Model PMD1204PPB1-A has blades with rotation speeds of 14,500 RPM and 9,500 RPM, respectively. This allows the counter-rotating fan module to produce a differential pressure not typically seen in fan designs. The preferred counter-rotating fan module can produce a maximum differential pressure of almost 2 inches of water. Stacking two counter-rotating fan modules in series continues the clockwise to counter-clockwise rotation progression as well the varying rotation speeds, and is quite capable of producing a differential pressure approaching 4 inches of water.

The inlet jet cross-sectional area of prior art 0.1 CFM particle sensors varies from approximately 0.5 mm$^2$ to 3 mm$^2$. Because this is the smallest physical restriction in the particle sensor system, it produces the largest pressure drop when the airflow is drawn through it. A feature of the invention is that the cross-sectional area of inlet jet nozzle 13 is enlarged, for example, to 4 mm$^2$ or greater. Testing has shown that a 4 mm$^2$ inlet jet area produces a pressure drop of less than 0.5 inches of water.

The prior art 0.1 CFM flow rate particle sensor inlet tubing sizes are ⅛ inch (3.2 mm) and ¼ inch (6.4 mm) inner diameter (ID). The inlet tubing cross-sectional area of prior art particle sensors ranges from typically 7.92 mm$^2$ for ⅛ inch ID tubing to 31.67 mm$^2$ for ¼ inch ID tubing. It is common to operate particle sensors with anywhere between 0 and 5 feet of inlet tubing. The pressure drop created by sample air flowing down this inlet tubing is the second largest pressure drop in the particle sensor system. A feature of the invention is that the inlet tubing pressure drop is controlled to accommodate an axial fan. Utilizing a ¼-inch inner diameter inlet tubing diameter produces a 0.1 CFM flow rate pressure drop of well less than 0.2 inches of water for a typical 5-foot length. There are other lesser pressure drops in the air flow system; however, using conventional tubing lengths, the invention provides a 0.1 CFM flow rate particle sensor that has a total system pressure drop of less than 1.25 inches of water.

The inlet jet cross-sectional area of prior art 1.0 CFM particle sensors vanes from approximately 5 mm$^2$ to 20 mm$^2$. Because this is the smallest physical restriction in the particle sensor system, it produces the largest pressure drop when the airflow is drawn through it. According to the invention, the inlet jet cross-sectional area for a 1.0 CFM particle sensor is 25 mm$^2$ or greater. Testing has shown that a 25 mm$^2$ inlet jet area produces a pressure drop of less than 1 inch of water. Testing has shown that a 30 mm$^2$ inlet jet area approaches 0.5 inches of water pressure drop. Thus, a particle sensor according to the invention has an insignificant inlet jet pressure drop for the available 2 inches of differential pressure produced by a counter-rotating fan module.

The most common prior art 1.0 CFM flow rate particle sensor inlet tubing sizes are ¼ inch (6.4 mm) and ⅜ inch (9.5 mm) inner diameter (ID). The inlet tubing cross-sectional area of these prior art particle sensors ranges typically from 31.67 mm$^2$ for ¼ inch ID tubing to 71.26 mm$^2$ for ⅜ inch ID tubing. It is common to operate particle sensors with anywhere between 0 and 5 feet of inlet tubing. The pressure drop created by sample air flowing down this inlet tubing is the second largest pressure drop in the particle sensor system. According to the invention, the inlet tubing pressure drop is also made larger to accommodate a counter-rotating fan module. As known by those skilled in the art, to minimize transport loss of large particles, it is recommended that the inlet tubing produce turbulent air flow with a Reynolds number of greater than 3000. This can be used as a guideline for establishing a maximum inlet tubing diameter for any given flow rate. At 1.0 CFM flow rate, the inlet tubing can have an inner diameter of 12 mm while still maintaining a Reynolds number of greater than 3000. This tubing diameter of conventional length produces a 1.0 CFM flow rate pressure drop of well less than 1 inch of water. There are other lesser pressure drops; however, a 1.0 CFM flow rate particle sensor according to the invention has a total system pressure drop of 2 inches of water or less.

Since nozzle 130 of the particle sensor according to the invention is larger, the height of focused gas flow 138 across sample chamber 135 will also be larger. It is a feature of the invention that the height of the gas flow jet in the vertical direction in FIG. 3 is 2.5 millimeters or larger. A related feature of the invention is that the effective height of laser beam 136 in the vertical direction in FIG. 3 is also substantially 2.5 millimeters or larger. The term "effective height" is used here as it is used in the art. As known in the art, a laser beam height in principal extends to infinity, but the effective height is the height over which the beam has enough energy to be effective in detecting particles. This height is generally referred to as the half-width of the laser beam, that is, the width at which the beam decreases in energy by one-half from the center of the beam. Another feature of the invention is that laser 134 of the particle counter according to the invention is preferably a 50 mw (milliwatts) to 100 mw laser. More preferably, laser 134 produces 50 mw (milliwatts) to 100 mw of power in the visible beam, and most preferably at substantially 660 nanometer wavelength. Such a laser provides ample power across the entire effective beam height for a laser beam of height of 2.5 millimeters and more.

A feature of the particle sensor and particle counter designs according to the invention is decreased cost. The previous cost per sample location of $500 to $700 is preferably decreased to less than $100 by the invention. Another feature of the invention is decreased size. The previously mentioned Sunon high static pressure fan module measures only 40 mm by 40 mm by 28 mm. This in much smaller than the air moving apparatus used in prior art instruments. The previously mentioned Sunon counter-rotating fan module measures only 40 mm by 40 mm by 56 mm. This is less than ¼ the size of air moving apparatus used in prior art instruments. Yet another feature of the invention is decreased weight. The Sunon fan modules weigh less than 88.5 grams. This is less than ¼ the weight of air moving apparatus used in prior art particle sensors. Yet another feature of the invention is decreased power consumption. Operating at a maximum power of 16.8 W, the technology according to the invention consumes far less power than previous air moving apparatus. A further feature of the invention is the longevity of the fan modules. With a MTTF (mean time to failure) time of typically 30,000 hours, the fan modules according to the invention are ideally suited for use in a particle counting instrument.

There has been described a novel particle sensor and particle counter system that have a much lower total system pressure drop through the airflow system. It should be understood that the particular embodiments shown in the drawings and described within this specification are for purposes of example and should not be construed to limit the invention, which will be described in the claims below. For example, while the invention has been described in terms of air particle sensors and particle counters, it may be employed with any gas. That is, the word "gas" may be substituted anyplace in this disclosure that the word "air" appears. Similarly, the term "gas" when applied to the fluid in which the particles are suspended as used herein is also intended to include particle sensors or particle counters referred to as "aerosol particle counters" in the art. Further, it is evident that those skilled in the art may now make numerous uses and modifications of the specific embodiments described without departing from the inventive concepts. For example, although the invention has been described in terms of 0.1 CFM and 1.0 CFM particle sensors and particle counters, the invention may be applied to particle sensors and particle counters with any flow rate. It is also evident that the methods recited may, in many instances, be performed in a different order, or equivalent structures and processes may be substituted for the various structures and processes described. Consequently, the invention is to be construed as embracing each and every novel feature and novel combination of features present in and/or possessed by the invention herein described.

What is claimed as new and desired to be protected by Letters Patent of the United States is:

1. An optical particle sensor for optically detecting unconstrained particles suspended in a flowing gas, said optical particle sensor comprising:
   a sample chamber having a gas inlet and a gas outlet, wherein said gas inlet includes an inlet jet nozzle;
   a gas flow system comprising a high static pressure axial fan or a counter rotating axial fan for flowing gas from said gas inlet through said inlet jet nozzle and said sample chamber to said gas outlet;
   a source of light;
   an optical system directing said light through said sample chamber;
   an optical collection system located to collect light scattered by said particles in said gas flowing through said sample chamber; and
   a detection system located to detect light collected by said optical collection system, said detection system including an optical detector producing an electric signal characteristic of said particles;
   wherein the total pressure drop through said inlet jet nozzle is 3 inches of water or less.

2. An optical particle sensor as in claim 1 wherein said total pressure drop through said inlet jet nozzle is 2 inches of water or less.

3. An optical particle sensor as in claim 1 wherein said total pressure drop through said inlet jet nozzle is 1 inches of water or less.

4. An optical particle sensor as in claim 1 wherein said gas flow system comprises a plurality of high static pressure or counter-rotating axial fans.

5. An optical particle sensor as in claim 1 wherein said gas flow system has a gas flow of substantially 0.1 GEM and said inlet jet nozzle has a cross-sectional area of 4 mm$^2$ (millimeter squared) or larger.

6. An optical particle sensor as in claim 5 wherein said gas flow system comprises inlet tubing having an inner diameter of 6.4 mm or larger.

7. An optical particle sensor as in claim 1 wherein said gas flow system has a gas flow of substantially 1 CFM and said inlet jet nozzle has a cross sectional area of 25 mm$^2$ or larger.

8. An optical particle sensor as in claim 7 wherein said gas flow system comprises inlet tubing having an inner diameter of 9.5 mm or larger.

9. An optical particle sensor as in claim 7 wherein said gas flow system comprises inlet tubing having an inner diameter of 12 mm or larger.

10. An optical particle sensor as in claim 1 wherein said gas flow system has a gas flow of substantially 1 CFM and said inlet jet nozzle has a cross-sectional area of 30 mm$^2$ or larger.

11. An optical particle sensor as in claim 1 wherein said source of light comprises a laser having a power of fifty milliwatts or greater.

12. An optical particle sensor as in claim 1 wherein said source of light comprises a laser having a power of a hundred milliwatts or greater.

13. An optical particle sensor as in claim 1 wherein said optical particle sensor consumes a power of 16.8 W or less.

14. An optical particle counter system including a plurality of particle sensors, each particle sensor comprising:
   a sample chamber having a gas inlet and a gas outlet, wherein said gas inlet includes an inlet jet nozzle;
   a gas flow system comprising a high static pressure axial fan or a counter rotating axial fan for flowing gas from said gas inlet through said inlet jet nozzle and said sample chamber to said gas outlet;
   a source of light;
   an optical system directing said light through said sample chamber;
   an optical collection system located to collect light scattered by said particles in said gas flowing through said sample chamber; and
   a detection system located to detect light collected by said optical collection system, said detection system including an optical detector producing an electric signal characteristic of said particles;
   wherein the total pressure drop through said inlet jet nozzle is 3 inches of water or less.

15. An optical particle sensor for optically detecting unconstrained particles suspended in a flowing gas, said optical particle sensor comprising:
   a sample chamber having a gas inlet and a gas outlet, wherein said gas inlet includes an inlet jet nozzle;
   a gas flow system comprising a high static pressure axial fan or a counter-rotating axial fan for flowing said gas from said gas inlet through said inlet jet nozzle and said sample chamber to said gas outlet, said gas flow system having a flow rate of substantially 0.1 CFM (cubic feet per minute) and said inlet jet nozzle having a cross-sectional area of 4 mm$^2$ (millimeters squared) or larger;
   a source of light;
   an optical system directing said light through said sample chamber;
   an optical collection system located to collect light scattered by said particles in said gas flowing through said sample chamber; and
   a detection system located to detect light collected by said optical collection system, said detection system including an optical detector producing an electric signal characteristic of said particles.

16. An optical particle sensor as in claim 15 wherein said optical particle sensor consumes a power of 16.8 W or less.

17. An optical particle sensor for optically detecting unconstrained particles suspended in a flowing gas, said optical particle sensor comprising:
   a sample chamber having a gas inlet and a gas outlet, wherein said gas inlet includes an inlet jet nozzle;
   a gas flow system comprising a high static pressure axial fan or a counter-rotating axial fan for flowing said gas from said gas inlet through said inlet jet nozzle and said sample chamber to said gas outlet, said gas flow system having a flow rate of substantially 1 CFM (cubic feet per minute) and a gas said inlet jet nozzle having a cross-sectional area of 25 mm$^2$ (millimeters squared) or larger;
   a source of light;
   an optical system directing said light through said sample chamber;
   an optical collection system located to collect light scattered by said particles in said gas flowing through said sample chamber; and a detection system located to detect light collected by said optical collection system, said detection system including an optical detector producing an electric signal characteristic of said particles.

18. An optical particle sensor as in claim 17 wherein said optical particle sensor consumes a power of 16.8 W or less.

19. A method of detecting unconstrained particles in a flowing gas, said method comprising:
   flowing said gas containing said unconstrained particles using a counter-rotating axial fan;
   directing a laser beam through said gas flow;
   collecting light scattered by said particles in said gas; and
   detecting said collected light and outputting a signal that is characteristic of a parameter of said particles.

20. A method of detecting unconstrained particles in a flowing gas, said method comprising:
   flowing said gas containing said unconstrained particles from a gas inlet through a sample chamber to a gas outlet using a high static pressure axial fan or a counter-rotating axial fan, said gas inlet having a total pressure drop of 3 inches of water or less;
   directing a laser beam through said gas flow;
   collecting light scattered by said particles in said gas; and
   detecting said collected light and outputting a signal that is characteristic of a parameter of said particles.

21. A method as in claim 20 wherein said total pressure drop through said gas inlet is 2 inches of water or less.

22. A method as in claim 20 wherein said total pressure drop through said gas inlet is 1 inches of water or less.

23. A method as in claim 20 wherein said directing comprises forming a laser beam having an effective beam height of 2.5 mm or greater.

24. A method as in claim 20 wherein said directing comprises forming a laser beam having a power of 50 milliwatts or greater.

25. A method as in claim 20 wherein said gas inlet includes an inlet jet nozzle.

26. A method as in claim 20 wherein said flowing gas containing said unconstrained particles has a height of 2.5 mm or greater.

27. A method of detecting unconstrained particles in a flowing gas, said method comprising:
   flowing said gas containing said unconstrained particles using a high static pressure axial fan;
   directing a laser beam through said gas flow;
   collecting light scattered by said particles in said gas; and
   detecting said collected light and outputting a signal that is characteristic of a parameter of said particles.

28. An optical particle sensor for optically detecting unconstrained particles suspended in a flowing gas, said optical particle sensor comprising:
   a sample chamber having a gas inlet and a gas outlet, wherein said gas inlet includes an inlet jet nozzle;
   a gas flow system comprising a high static pressure axial fan for flowing gas from said gas inlet through said inlet jet nozzle and said sample chamber to said gas outlet;
   a source of light;
   an optical system directing said light through said sample chamber;
   an optical collection system located to collect light scattered by said particles in said gas flowing through said sample chamber; and
   a detection system located to detect light collected by said optical collection system, said detection system including an optical detector producing an electric signal characteristic of said particles;
   wherein the total pressure drop through said inlet jet nozzle is 3 inches of water or less.

29. An optical particle sensor for optically detecting unconstrained particles suspended in a flowing gas, said optical particle sensor comprising:
   a sample chamber having a gas inlet and a gas outlet, wherein said gas inlet includes an inlet jet nozzle;
   a gas flow system comprising a counter-rotating axial fan for flowing gas from said gas inlet through said inlet jet nozzle and said sample chamber to said gas outlet;
   a source of light;
   an optical system directing said light through said sample chamber;
   an optical collection system located to collect light scattered by said particles in said gas flowing through said sample chamber; and
   a detection system located to detect light collected by said optical collection system, said detection system including an optical detector producing an electric signal characteristic of said particles;
   wherein the total pressure drop through said inlet jet nozzle is 3 inches of water or less.

* * * * *

UNITED STATES PATENT AND TRADEMARK OFFICE
CERTIFICATE OF CORRECTION

| | | |
|---|---|---|
| PATENT NO. | : 7,667,839 B2 | Page 1 of 1 |
| APPLICATION NO. | : 11/393475 | |
| DATED | : February 23, 2010 | |
| INVENTOR(S) | : Thomas Bates | |

It is certified that error appears in the above-identified patent and that said Letters Patent is hereby corrected as shown below:

At column 11, in Claim 5, line 44, delete "GEM" and replace with --CFM--.

At column 12, in Claim 17, line 60, delete "a gas".

Signed and Sealed this

Third Day of August, 2010

David J. Kappos
*Director of the United States Patent and Trademark Office*